United States Patent
Hong et al.

(10) Patent No.: US 12,037,610 B2
(45) Date of Patent: *Jul. 16, 2024

(54) METHODS FOR PREPARING N-ACETYL-L-METHIONINE

(71) Applicant: CJ CHEILJEDANG CORPORATION, Seoul (KR)

(72) Inventors: So Yeon Hong, Seoul (KR); Jinseung Park, Gyeonggi-do (KR); Hye Min Park, Gyeongsangnam-do (KR); Su Jin Choi, Daegu (KR); Jun Ok Moon, Gyeonggi-do (KR); Sung Gun Lee, Busan (KR); Jinwoo Jeon, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 10 days.

This patent is subject to a terminal disclaimer.

(21) Appl. No.: 17/452,565

(22) Filed: Oct. 27, 2021

(65) Prior Publication Data

US 2022/0042000 A1 Feb. 10, 2022

Related U.S. Application Data

(62) Division of application No. 16/319,511, filed as application No. PCT/KR2017/007770 on Jul. 19, 2017, now abandoned.

(30) Foreign Application Priority Data

Jul. 20, 2016 (KR) .......................... 10-2016-0092228

(51) Int. Cl.
| | |
|---|---|
| *C12N 9/10* | (2006.01) |
| *C12N 15/63* | (2006.01) |
| *C12N 15/70* | (2006.01) |
| *C12N 15/77* | (2006.01) |
| *C12N 15/81* | (2006.01) |
| *C12P 13/12* | (2006.01) |

(52) U.S. Cl.
CPC ............ *C12N 9/1025* (2013.01); *C12N 9/10* (2013.01); *C12N 15/63* (2013.01); *C12N 15/70* (2013.01); *C12N 15/77* (2013.01); *C12N 15/81* (2013.01); *C12P 13/12* (2013.01); *C12Y 203/01001* (2013.01)

(58) Field of Classification Search
CPC ............................... C12N 9/1025; C12P 13/12
See application file for complete search history.

(56) References Cited

U.S. PATENT DOCUMENTS

| | | | |
|---|---|---|---|
| 8,143,031 B2 | 3/2012 | Figge et al. | |
| 10,750,762 B2 * | 8/2020 | Jeon | ......................... C12P 13/12 |

FOREIGN PATENT DOCUMENTS

| | | |
|---|---|---|
| JP | 2012-500623 A | 1/2012 |
| KR | 10-2011-0042383 | 4/2011 |
| WO | WO 01/00804 A2 | 1/2001 |
| WO | WO 20113/190343 | 12/2013 |

OTHER PUBLICATIONS

Fransceus. J Ind Microbiol Biotechnol. May 2017;44(4-5):687-695.*
Sanavia. Computational and Structural Biotechnology Journal, vol. 18, 2020, pp. 1968-1979.*
Studer. Residue mutations and their impact on protein structure and function: detecting beneficial and pathogenic changes. Biochem. J. (2013) 449, 581-594.*
Amos, H. E., "Methionine, DL-Homocysteine Thiolactone And N-Acetyl-DL-Methionine for Ruminants" Journal of Animal Science, vol. 39, No. 3, 1974, pp. 612-617.
Database: uniprot, Accession No. B1J5W5 (B1J5W5_PSEPW), Title: GCN5-related N-acetyltransferase (Apr. 29, 2008).
Davies, A.M., "L-Methionine Sulfoximine, but not Phosphinothricin, Is a Substrate for an Acetyltransferase (Gene PA4866) from *Pseudomonas aeruginosa*: Structural and Functional Studies", Biochemistry, 2007, pp. 1829-1839.
ECMDB Accession Nos. (ECMDB23042) (M2MDB003432) N-Acetyl-L-methionine Oct. 10, 2012.
Feb. 4, 2020 Office Action issued in connection with Japanese Patent Application No. 2019-502580.
International Search Report issued Oct. 26, 2017 in connection with PCT International Application No. PCT/KR2017/007770.
Jan. 12, 2021 Office Action issued in connection with New Zealand Patent Application No. 750131.
Jan. 21, 2020 Extended European Search Report issued in connection with European Patent Application No. EP 17831346.
NCBI, GenBank Accession No. AF045988, Jan. 30, 2014.
NCBI, GenBank Accession No. KHL74469, Dec. 16, 2014.
NCBI Reference Sequence: WP 012316437.1: N-acetyltransferase [Pseudomonas putida] May 25, 2013.
NCBI Reference Sequence: WP 011014038.1: acetyltransferase [Corynebacterium glutamicum] May 24, 2013.
NCBI Reference Sequence: WP 039602721.1: acetyltransferase [ Pseudomonas putida] Jan. 11, 2015.

(Continued)

*Primary Examiner* — Yong D Pak
(74) *Attorney, Agent, or Firm* — John P. White

(57) ABSTRACT

The present disclosure relates to a polypeptide having an acyltransferase activity or a microorganism including the same; a composition for preparing N-acetyl-L-methionine, the composition including the polypeptide or microorganism; and a method of preparing N-acetyl-L-methionine using the polypeptide or microorganism. Further, the present disclosure relates to a polynucleotide encoding the polypeptide and an expression vector including the polynucleotide. Since the microorganism including a novel acyltransferase according to the present disclosure has enhanced acyltransferase activity, this microorganism can be efficiently used for producing N-acetyl-L-methionine by acetylating L-methionine.

5 Claims, No Drawings

Specification includes a Sequence Listing.

(56) References Cited

OTHER PUBLICATIONS

NCBI Reference Sequence: WP 010886629.1: phosphinothricin Acetyltransferase [*Bacillus subtilis*] May 15, 2013.
NCBI Reference Sequence: WP 012017494.1: N-acetyltransferase [*Enterobacter* sp. 638] May 25, 2013.
NCBI Reference Sequence: WP 014283831.1: N-acetyltransferase [*Pseudovibrio* sp. FO-BEG1] May 28, 2013.
NCBI Reference Sequence: XP 500352.1: YALI0B00638p [*Yarrowia lipolytica*] Oct. 29, 2008.
NCBI Reference Sequence: WP 012017494.1: Gnat family N-acetyltransferase [*Enterobacter* sp. 638] May 15, 2021.
NCBI Reference Sequence: WP 014283831.1: Gnat family N-acetyltransferase [*Pseudovibrio* sp. FO-BEG1] May 15, 2021.
NCBI Reference Sequence: XP 500352.1: YALI0B00638p [*Yarrowia lipolytica* CLIB122] Jun. 6, 2017.
Ouoba et al., "Degradation of proteins during the fermentation of African locust bean (*Parkia biglobosa*) by strains of Bacillus subtilis and Bacillus pumilus for production of Soumbala," Journal of Applied Microbiology, vol. 94(3), pp. 396-402.
Sep. 29, 2021 Office Action issued in connection with Indian Patent Application No. 201917003181.
Aug. 1, 2023 Hearing Notice Issued by Indian Patent Office in connection with Indian Patent Application No. 201917003181.

\* cited by examiner

METHODS FOR PREPARING N-ACETYL-L-METHIONINE

CROSS-REFERENCE TO RELATED APPLICATIONS

This application is a divisional of U.S. application Ser. No. 16/319,511, filed Jan. 22, 2019, which is a § 371 national stage of PCT International Application No. PCT/KR2017/007770, filed Jul. 19, 2017, claiming priority of Korean Patent Application No. 10-2016-0092228, filed Jul. 20, 2016, the contents of each of which in its entirety is hereby incorporated by reference into the subject application.

REFERENCE TO SEQUENCE LISTING

This application incorporates-by-reference nucleotide and/or amino acid sequences which are present in the file named "211027_90809-Z_Substitute_Sequence_Listing_JMP.txt," which is 21 kilobytes in size, and which was created Oct. 26, 2021 in the IBM-PC machine format, having an operating system compatibility with MS-Windows, which is contained in the text file filed Oct. 27, 2021 as part of this application.

TECHNICAL FIELD

The present disclosure relates to a polypeptide having an acyltransferase activity or a microorganism including the same; a composition for preparing N-acetyl-L-methionine, the composition including the polypeptide or microorganism; and a method of preparing N-acetyl-L-methionine using the polypeptide or microorganism. Further, the present disclosure relates to a polynucleotide encoding the polypeptide and an expression vector including the polynucleotide.

BACKGROUND ART

N-Acetylmethionine, which is a derivative of methionine, has similar efficacy to methionine, but it can reduce methionine-specific flavors and can be added in a large amount compared to methionine when added to foods. In the case of animals having a rumen, when methionine is used as a feed additive, it is first used by rumen microorganisms and thus is not absorbed by the animals, whereas N-acetylmethionine is a rumen-protected amino acid that is absorbed after passing through the rumen and reaching the intestine. The degradation resistance of N-acetyl-DL-methionine at the rumen is known (Amos et al., Journal of Animal Science, 1974, 39(3), pp. 612-617). Accordingly, the production of N-acetylmethionine has industrial value, and particularly, it is preferable to provide an L-type amino acid having a high absorption rate and high bioavailability when used as a feed additive, and therefore research and development of N-acetyl-L-methionine is required. In the case of enzymes reported to convert methionine to N-acetylmethionine, YncA of *Escherichia coli* is unique (U.S. Pat. No. 8,143,031 B2). In this document, it was found that acetyl-CoA was used indirectly through a DTNB analysis method to measure the inactivity of YncA, and it was not found that N-acetylmethionine was produced. Further, it has not been found that N-acetylmethionine is actually produced by the transformant transformed by YncA.

DISCLOSURE

Technical Problem

The present inventors have conducted continuous efforts to produce N-acetyl-L-methionine through a microbial fermentation or an enzymatic reaction, and thus have searched for microorganisms capable of producing N-acetyl-L-methionine and discovered six new acyltransferases. Further, they have found that N-acetyl-L-methionine can be produced economically at a high concentration using the novel acyltransferase of the present disclosure or a microorganism expressing the novel acyltransferase, as compared with a known acyltransferase. Based on this finding, the present disclosure has been completed.

Technical Solution

An object of the present disclosure is to provide a microorganism having an acyltransferase activity, the microorganism including a polypeptide represented by an amino acid sequence of any one of SEQ ID NOS. 1 to 6 or an amino acid sequence having 90% or more homology to the amino acid sequence.

Another object of the present disclosure is to provide a polypeptide having an acetyltransferase activity, the polypeptide being represented by an amino acid sequence of any one of SEQ ID NOS. 1 to 6 or an amino acid sequence having 90% or more homology to the amino acid sequence.

Still another object of the present disclosure is to provide a polynucleotide encoding the polypeptide.

Still another object of the present disclosure is to provide an expression vector including the polynucleotide.

Still another object of the present disclosure is to provide a composition for preparing N-acetyl-L-methionine from L-methionine, the composition including, as an active ingredient: (i) the microorganism or a culture thereof; (ii) the polypeptide; or a combination thereof.

Still another object of the present disclosure is to provide a method of preparing N-acetyl-L-methionine, including: acetylating L-methionine using (i) the microorganism or a culture thereof; (ii) the polypeptide; or a combination thereof.

Advantageous Effects

Since the microorganism including a novel acyltransferase according to the present disclosure has enhanced acyltransferase activity, this microorganism can be efficiently used for producing N-acetyl-L-methionine by acetylating L-methionine.

BEST MODE FOR INVENTION

In order to accomplish the above objects, an aspect of the present disclosure provides a microorganism having acyltransferase activity, the microorganism including a polypeptide represented by an amino acid sequence of any one of SEQ ID NOS. 1 to 6 or an amino acid sequence having 90% or more homology thereto.

The term "acyltransferase" used in the present disclosure refers to an enzyme having an activity of transferring an acyl group from a donor to a receptor. In the present disclosure, the donor is not limited as long as it can provide an acyl group to a receptor, but may specifically be acetyl coenzyme A (acetyl-CoA). Further, as used herein, the receptor is not limited as long as it can receive an acyl group from a donor, but may specifically be L-methionine.

Specifically, the acyltransferase may be derived from genus *Pseudomonas*, genus *Bacillus*, genus *Enterobacter*, genus *Pseudovibrio*, genus *Yarrowia*, or genus *Corynebacterium*. More specifically, the acyltransferase may be derived from *Pseudomonas putida*, *Bacillus subtilis*, *Enterobacter* sp. 638, *Pseudovibrio* sp. FO-BEG 1, *Yarrowia lipolytica*, or *Corynebacterium glutamicum*.

Specifically, the acyltransferase may be a polypeptide having an amino acid sequence of any one of SEQ ID NOS. 1 to 6. Further, the acyltransferase may be a polypeptide having an amino acid sequence having 70% or more, 80% or more, or 90% or more homology to an amino acid sequence of any one of SEQ ID NOS. 1 to 6 and having an acyltransferase activity substantially the same as or corresponding to that of the amino acid sequence of any one of SEQ ID NOS. 1 to 6. Further, the amino acid sequence having such homology and having an acyltransferase activity substantially the same as or corresponding to that of the amino acid sequence of any one of SEQ ID NOS. 1 to 6 may be an amino acid sequence, a part of which is deleted, transformed, substituted, or added. It is obvious that this case may also be included in the scope of the present disclosure.

The term "homology" used in the present disclosure refers to the degree of identity of base or amino acid residues between sequences after aligning both amino acid sequences or base sequences of a gene encoding a polypeptide in a specific comparison region to be matched with each other as much as possible. When the homology is sufficiently high, expression products of the corresponding gene may have the same or similar activity. The percentage of the sequence identity can be determined using a known sequence comparison program, for example, BLAST (NCBI), CLC Main Workbench (CLC bio), MegAlign (DNASTAR Inc), or the like.

The term "microorganism having an acyltransferase activity" used in the present disclosure refers to a microorganism producing an acyltransferase in vivo or in vitro. Specifically, since the microorganism of the present disclosure includes a polypeptide having an amino acid sequence of any one of SEQ ID NOS. 1 to 6 and thus has an acyltransferase activity, it can transfer an acyl group to a receptor. More specifically, the microorganism of the present disclosure has acetyltransferase activity to L-methionine and thus can produce N-acetyl-L-methionine. In the present disclosure, N-acetyl-L-methionine and N-acetylmethionine are used interchangeably.

Additionally, the microorganism of the present disclosure includes not only microorganisms which inherently contain a polypeptide having an amino acid sequence of any one of SEQ ID NOS. 1 to 6, but also microorganisms in which the activity of the polypeptide is enhanced as compared with an intrinsic activity. That is, the production capacity of the acyltransferase can be imparted or enhanced by natural or anthropogenic mutagenesis or species modification. The term "enhancement" of polypeptide activity, as used herein, refers to improving the active state of the polypeptide included in the microorganism. Enhancement of polypeptide activity is not limited as long as it can enhance the activity of each polypeptide, such as the enhancement of the activity of the target polypeptide, as compared with a natural state or to a non-variation state of the polypeptide. For example, the enhancement of polypeptide activity may be performed by a method selected from i) increasing the number of copies of a polynucleotide encoding each polypeptide, ii) modifying an expression sequence to increase the expression of the polynucleotide, iii) modifying the polynucleotide sequence on the chromosome to enhance the activity of each polypeptide, and iv) a combination thereof. Specifically, the enhancement of polypeptide activity may be performed by a method selected from a method of inserting a polynucleotide including a nucleotide sequence encoding each polypeptide into a chromosome, a method of introducing the polynucleotide into a microorganism through a vector system, a method of introducing a promoter exhibiting an improved activity upstream of a base sequence encoding each polypeptide or introducing each of the mutated polypeptides into a promoter, a method of modifying the nucleotide sequence in the 5'-UTR region, and a method of introducing a mutant of the base sequence encoding each polypeptide, but the present disclosure is not limited thereto.

Further, in the present disclosure, the microorganism having an acyltransferase activity may be used regardless of the origin of the microorganism as long as it has an acyltransferase activity. For example, the microorganism may be *Escherichia* sp., *Corynebacterium* sp., *Saccharomyces* sp., or *Yarrowia* sp. More specifically, the microorganism may be *Escherichia coli*, *Corynebacterium glutamicum*, *Saccharomyces cerevisiae*, or *Yarrowia lipolytica*, but is not limited thereto.

Further, in the present disclosure, the microorganism having an acyltransferase activity may be a microorganism having enhanced cell membrane permeability of a donor and/or a receptor. As the method of increasing the cell membrane permeability, a known method may be used. Specifically, processes of freezing and thawing the microorganism may be repeated, but the present disclosure is not limited thereto.

Further, in the present disclosure, the microorganism having an acyltransferase activity may biosynthesize a receptor to which an acyl group is transferred from a donor, but the present disclosure is not limited thereto. Specifically, the microorganism of the present disclosure may produce N-acetyl-L-methionine even when it is cultured in a medium to which L-methionine is not added because it has an ability of producing L-methionine that is an acceptor of an acyl group.

Further, in the present disclosure, the microorganism having an acyltransferase activity may be a mutant microorganism into which a known mutation is introduced with respect to a related mechanism such as a biosynthesis-related pathway or a substrate releasing capacity-related mechanism in order to enhance N-acetyl-L-methionine production ability separately from the acyltransferase.

An aspect of the present disclosure provides a polypeptide having an acetyltransferase activity, the polypeptide being represented by an amino acid sequence of any one of SEQ ID NOS. 1 to 6 or an amino acid sequence having 90% or more homology to the amino acid sequence. Specifically, the acetyltransferase activity may be an acetyltransferase activity to L-methionine.

The polypeptide is as described above.

Another aspect of the present disclosure provides a polynucleotide encoding the polypeptide having an acetyltransferase activity, the polypeptide being represented by an amino acid sequence of any one of SEQ ID NOS. 1 to 6 or an amino acid sequence having 90% or more homology to the amino acid sequence. The polypeptide is as described above.

For example, the polynucleotide may be a base sequence of any one of SEQ ID NOS. 7 to 12, but is not limited thereto. Further, the polynucleotide may include a base sequence encoding the same amino acid sequence due to genetic code degeneracy, and a mutant thereof. For example, the polynucleotide may be modified to have an optimal codon depending on the microorganism used.

Specifically, the polynucleotide may be a base sequence encoding an amino acid sequence having 70% or more, 80% or more, or 90% or more homology to the above base sequence and having an acyltransferase activity substantially the same as or corresponding to that of the above base sequence. Further, the polynucleotide may be a probe that can be prepared from a known gene sequence, for example, it may be a sequence encoding a polypeptide having an acyltransferase activity by hybridization with a complementary sequence to all or part of the base sequence under stringent conditions. Here, the "stringent conditions" refer to conditions where a specific hybrid is formed and a non-specific hybrid is not formed. For example, the stringent conditions may include a condition where genes having high homology, for example, genes having 80% or more, specifically 90% or more, more specifically 95% or more, further specifically 97% or more, or particularly specifically 99% or more homology are hybridized and genes having lower homology are not hybridized, and a condition where cleaning is performed one time, specifically two or three times under a salt concentration and temperature corresponding to 60° C., 1×SSC, 0.1% SDS, specifically 60° C., 0.1×SSC, 0.1% SDS, and more specifically 68° C., 0.1× SSC, 0.1% SDS, which are cleaning conditions for conventional hybridization, (Sambrook et al., Molecular Cloning: A Laboratory Manual, 3rd Ed., Cold Spring Harbor Laboratory Press, Cold Spring Harbor, N.Y. (2001)).

The probe used in the hybridization may be a part of a complementary sequence of the base sequence. This probe may be prepared by PCR using a gene fragment including such a base sequence as a template by using an oligonucleotide prepared based on a known sequence as a primer. For example, as the probe, a gene fragment having a length of about 300 bp may be used. More specifically, when a gene fragment having a length of about 300 bp is used as the probe, as cleaning conditions for hybridization, 50° C., 2×SSC, and 0.1% SDS are exemplified.

Genes, polypeptide sequences encoded by the genes, and promoter sequences, which are used in the present disclosure, may be obtained from known databases, for example, GenBank of NCBI. However, the present disclosure is not limited thereto.

Still another aspect of the present disclosure provides an expression vector including the polynucleotide.

The expression vector including the polynucleotide according to the present disclosure is an expression vector capable of expressing a target protein in a suitable host cell, and refers to a polynucleotide product including an essential control element operably linked so as to express a polynucleotide insert. Target proteins may be obtained by transforming or transfecting the prepared recombination vector in the host cell.

The expression vector including the polynucleotide according to the present disclosure is not particularly limited, but includes *Escherichia coli*-derived plasmids (pYG601BR322, pBR325, pUC118, and pUC119), *Bacillus subtilis*-derived plasmids (pUB110 and pTP5), yeast-derived plasmids (YEp13, YEp24, and YCp50), and Ti-plasmids that can be used for *agrobacterium*-mediated transformation. Specific examples of phage DNA include λ-phages (Charon4A, Charon21A, EMBL3, EMBL4, lambda gt10, lambda gt11, and lambda ZAP). Further, virus vectors derived from animal viruses such as retrovirus, adenovirus, and vaccinia virus, insect viruses such as baculovirus, double-stranded plant virus (for example, CaMV), single-stranded virus, or Geminiviruses may also be used.

Moreover, as the vector of the present disclosure, a fusion plasmid (for example, pJG4-5) to which nucleic acid expression activating protein (for example, B42) is linked may be used. Further, in order to facilitate the purification of a target protein recovered in the present disclosure, the plasmid vector may further include other sequences as necessary. Such a fusion plasmid may include GST, GFP, His-tag, or Myc-tag as a tag, but the fusion plasmid of the present disclosure is not limited to the above examples.

Further, in the production of the fusion protein, a chromatography process may be used, and in particular, the fusion protein may be purified by affinity chromatography. For example, when glutathione-S-transferase is fused, glutathione, which is a substrate of this enzyme, may be used. When hexahistidine is used, a desired target protein can be easily recovered using a Ni-NTA His-conjugated resin column (Novagen, USA).

In order to insert the polynucleotide of the present disclosure as a vector, a method of cleaving purified DNA with a suitable restriction enzyme and inserting the cleaved DNA into a restriction site or a cloning site of an appropriate vector DNA may be used.

The polynucleotide encoding the polypeptide of the present disclosure may be operably linked to a vector. The vector of the present disclosure may additionally include a cis-element such as an enhancer, a splicing signal, a poly A addition signal, a selection marker, and a ribosome binding sequence (SD sequence), in addition to the promoter and nucleic acid of the present disclosure. Examples of the selection marker may include chloramphenicol resistance, ampicillin resistance, dihydrofolate reductase, and neomycin resistance, but additional components operably linked by the above examples are not limited. The term "transformation" as used herein refers to a phenomenon of introducing DNA into the host cell to allow the DNA to serve as a factor of a chromosome or to be replicated by chromosome integration completion and introducing external DNA into a cell to cause an artificial genetic change.

An expression vector including a polynucleotide encoding the polypeptide of the present disclosure or a part of the expression vector may be introduced into a host cell. Here, a part of the expression vector refers to a portion of the expression vector, the portion including a portion of the polynucleotide encoding the polypeptide of the present disclosure so as to impart the acyltransferase activity into the host cell. For example, T-DNA of Ti-plasmid transferred into the host cell in *agrobacterium*-mediated transformation may be exemplified, but the present disclosure is not limited thereto.

Any transformation method may be used for the transformation method of the present disclosure, and may be easily carried out according to a method known in the art. Generally, the transformation method may include a $CaCl_2$ precipitation method, a Hanahan method in which dimethyl sulfoxide (DMSO) is used as a reduction material in the $CaCl_2$ precipitation method to increase efficiency, an electroporation method, a $CaPO_4$ precipitation method, a protoplasm fusion method, a stirring method using silicon carbide fiber, an *agrobacterium*-mediated transformation method, a transformation method using PEG, a dextran sulfate-mediated transformation method, a lipofectamine-mediated transformation method, and a drying/inhibition-mediated transformation method. The method of transforming a vector including a polynucleotide encoding the polypeptide of the present disclosure is not limited to the above examples, and transformation or transfection methods commonly used in the art may be used without limitation.

The kind of host cells used in the preparation of a transformant in the present disclosure is not particularly limited as long as the polynucleotide of the present disclosure is expressed. Specific examples of the host cells used in the present disclosure may include bacteria of genus *Escherichia* such as *E. coli*; bacteria of genus *Bacillus* such as *Bacillus subtilis*; bacteria of genus *Pseudomonas* such as *Pseudomonas putida*; yeasts such as *Saccharomyces cerevisiae* and *Schizosaccharomyces pombe*; animal cells; plant cells; and insect cells. Specific examples of *Escherichia coli* strains that can be used in the present disclosure may include CL41(DE3), BL21, and HB101, and specific examples of *Bacillus subtilis* strains that can be used in the present disclosure may include WB700 and LKS87.

The transformant into which an expression vector including the polynucleotide of the present disclosure is introduced may be in the form of a transformed cell or an organism.

As the promoter in the present disclosure, any promoter may be used as long as it is capable of expressing the polynucleotide of the present disclosure in the host cell. For example, *Escherichia coli* or phage-derived promoters such as trp promoter, lac promoter, PL promoter, and PR promoter; *Escherichia coli*-infected or phage-derived promoters such as T7 promoter; CaMV35S, MAS or histone promoter; and cj7 promoter (Korean Patent Application Publication No. 10-2004-0107215) may be used. Further, artificially modified promoters such as tac promoter may also be used.

Still another aspect of the present disclosure provides a method of preparing N-acetyl-L-methionine, including: acetylating L-methionine using (i) the microorganism of the present disclosure or a culture thereof; (ii) the polypeptide of the present disclosure; or a combination thereof.

Specifically, the method includes: preparing N-acetyl-L-methionine, including: acetylating L-methionine using (i) the microorganism of the present disclosure or a culture thereof; (ii) the polypeptide of the present disclosure; or a combination thereof; and recovering N-acetyl-L-methionine, which is the acetylated L-methionine.

In the present disclosure, the "culturing" refers to growing the microorganism under suitably controlled environmental conditions.

The culturing process of the present disclosure may be performed according to a suitable medium and culture conditions, which are known in the art. Such a culturing process may be easily adjusted by those skilled in the art depending on the strain to be selected. In the above method, the process of culturing the microorganism is not particularly limited, but may be conducted by a batch culture method, a continuous culture method, or a fed-batch culture method, which is known in the art. The medium used for culturing the microorganism of the present disclosure and other culture conditions may be used without any particular limitation as long as it can be used for culturing general microorganisms. Specifically, the microorganism of the present disclosure may be cultured in a general medium including a carbon source, a nitrogen source, a phosphorus source, an inorganic compound, amino acid, and/or vitamin while controlling temperature, pH, and the like under aerobic conditions.

In the present disclosure, examples of the carbon sources may include, but are not limited to, carbohydrates such as glucose, fructose, sucrose, maltose, mannitol, and sorbitol; alcohols such as saccharide alcohol, glycerol, pyruvic acid, lactic acid, and citric acid; organic acids; and amino acids such as glutamic acid, methionine, and lysine. Further, natural nutrient sources such as starch hydrolysate, molasses, blackstrap molasses, rice bran, cassava, sugar cane residues, and corn immersion liquids may be used. Specifically, carbohydrates such as glucose and sterilized pretreated molasses (that is, molasses converted to reducing sugars) may be used, and suitable amounts of other carbon sources may be variously used without limitation. These carbon sources may be used alone or in a combination of two or more.

Examples of the nitrogen sources may include inorganic nitrogen sources such as ammonia, ammonium sulfate, ammonium chloride, ammonium acetate, ammonium phosphate, ammonium carbonate, and ammonium nitrate; and organic nitrogen sources, such as amino acids such as glutamic acid, methionine and glutamine, peptone, NZ-amine, meat extracts, yeast extracts, malt extracts, corn immersion liquids, casein hydrolysates, fish or degradation products thereof, and defatted soybean cake or degradation products thereof. These nitrogen sources may be used alone or in a combination of two or more. However, the present disclosure is not limited thereto.

Examples of the phosphorus sources may include potassium phosphate, potassium phosphite, and sodium-containing salts thereof. Examples of the inorganic compound may include sodium chloride, calcium chloride, iron chloride, magnesium sulfate, iron sulfate, manganese sulfate, and calcium carbonate, and may further include, but are not limited thereto, amino acids, vitamins, and/or suitable precursors. These media or precursors may be added to a culture in a batch or continuous manner, but are not limited thereto.

In the present disclosure, the pH of a culture may be adjusted by adding a compound such as ammonium hydroxide, potassium hydroxide, ammonia, phosphoric acid, or sulfuric acid to a culture in an appropriate manner during the culturing of microorganisms. Further, during the culturing of microorganisms, the formation of bubbles may be suppressed by using a defoaming agent such as aliphatic polyglycol ester. Further, oxygen or oxygen-containing gas may be injected into a culture in order to maintain the aerobic state of the culture, or nitrogen, hydrogen, or carbon dioxide gas may be injected into the culture in order to maintain the anaerobic and non-aerobic states of the culture without injecting the gas.

The temperature of the culture varies depending on the microorganism of the present disclosure. Specifically, the temperature thereof may be 20° C. to 50° C., more specifically, 25° C. to 40° C., but is not limited thereto. The culturing period may be continued until the amount of a desired useful material is obtained. Specifically, the culturing period may be 10 hours to 100 hours, but is not limited thereto.

Further, the term "culture" as used herein refers to a product obtained after culturing the microorganism of the present disclosure. The culture includes both a form containing microorganisms and a form in which microorganisms are removed by centrifugation or the like in a culture solution containing the microorganisms.

Further, in the present disclosure, L-methionine may be produced by the microorganism of the present disclosure or may be added to the medium.

Further, in the step of recovering N-acetyl-L-methionine in the present disclosure, targeted N-acetyl-L-methionine may be recovered from the culture solution using a suitable method known in the related art according to the method of culturing the microorganism of the present disclosure, for example, a batch culture method, a continuous culture method, or a fed-batch culture method. For example, centrifugation, filtration, anion exchange chromatography, crystallization, HPLC, and the like may be used, and a combination of suitable methods known in the art may be used.

The recovering step may include a separating step and/or a purifying step.

Still another aspect of the present disclosure provides a composition for preparing N-acetyl-L-methionine from L-methionine, the composition including, as an active ingredient: (i) the microorganism of the present disclosure or a culture thereof; (ii) the polypeptide of the present disclosure; or a combination thereof. The microorganism, culture, polypeptide, and N-acetyl-L-methionine are as described above.

MODE FOR INVENTION

Hereinafter, the present disclosure will be described in more detail with reference to Examples. However, these Examples are only illustrative of the present disclosure, and the scope of the present disclosure is not limited to these Examples.

Example 1: Selection of Novel Enzyme for Producing N-Acetylmethionine

Example 1-1: Selection of Microorganism for Producing N-Acetyl-L-Methionine

As microorganisms having an ability of producing N-acetyl-L-methionine, N-acetylmethionine spots, which are products, were confirmed from six kinds of randomly selected microorganism culture solutions (*Pseudomonas putida, Bacillus subtilis, Enterobacter* sp. 638, *Pseudovibrio* sp. FO-BEG1, *Yarrowia lipolytica* PO1f (ATCC MYA-2613™), and *Corynebacterium glutamicum* ATCC 13032).

Specifically, *Pseudomonas putida, Bacillus subtilis, Enterobacter* sp. 638, or *Yarrowia lipolytica* PO1f was inoculated in a 14 mL disposable culture tube containing 3 mL of a liquid YPD medium (1% yeast extract, 2% bactopeptone, 2% glucose), and was shake-cultured for 24 hours under conditions of 30° C. and 200 rpm to obtain a seed culture solution. 1 mL of the seed culture solution was inoculated in a 250 mL corner-baffle flask filled with 24 mL of the liquid YPD medium containing 0.5% (5 g/L) of methionine, and was shake-cultured for 24 hours under conditions of 30° C. and 200 rpm.

Further, *Pseudovibrio* sp. FO-BEG1 was inoculated in a 14 mL disposable culture tube containing 3 mL of a liquid BACTO Marine broth (Difco 2216) medium, and was shake-cultured for 24 hours under conditions of 28° C. and 200 rpm to obtain a seed culture solution. 1 mL of the seed culture solution was inoculated in a 250 mL corner-baffle flask filled with 24 mL of the liquid BACTO Marine broth (Difco 2216) medium containing 0.5% (5 g/L) of methionine, and was shake-cultured for 24 hours under conditions of 28° C. and 200 rpm.

Further, *Corynebacterium glutamicum* ATCC 13032 was inoculated in a 14 mL disposable culture tube containing 3 mL of a dedicated composite liquid medium (ingredients shown below), and was shake-cultured for 24 hours under conditions of 30° C. and 200 rpm to obtain a seed culture solution. 1 mL of the seed culture solution was inoculated in a 250 mL corner-baffle flask filled with 24 mL of the dedicated composite liquid medium containing 0.5% (5 g/L) of methionine, and was shake-cultured for 24 hours under conditions of 37° C. and 200 rpm.

<Composite Liquid Medium>

20 g glucose, 10 g peptone, 5 g yeast extract, 1.5 g urea, 4 g $KH_2PO_4$, 8 g $K_2HPO_4$, 0.5 g $MgSO_4 7H_2O$, 100 μg biotin, 1000 μg thiamine HCl, 2000 μg calcium pantothenate, 2000 μg nicotinamide, and 25 mg kanamycin (based on 1 L distilled water).

After completion of the culturing, the culture solution was left in an oven at 50° C. overnight to be concentrated, and 1 μL of the concentrated culture solution was analyzed using thin layer chromatography. 10 mM of a N-acetyl-L-methionine reagent (Sigma Aldrich 01310) was used as a control group. The same spot as the control group was confirmed from the culture liquid concentrate of the above six kinds of microorganisms.

From the above results, it was predicted that each of the six kinds of microorganisms having an ability of producing N-acetyl-L-methionine contains an acyltransferase including L-methionine as a substrate.

Example 1-2: Confirmation of Novel Acyltransferase Sequence

Methionine acyltransferase was selected from the six kinds of microorganisms selected in Example 1-1.

Heterogeneous homology searches for the selected proteins were performed by restricting the database to species of the microorganism based on an amino acid sequence with YncA known as a conventional methionine acyltransferase. As a result, all of the six kinds of searched enzymes were found to have low homology with the YncA amino acid sequence, and the homology of the *Enterobacter* sp. 63-derived acyltransferase sequence, which had the highest homology, was 82%. Homologies of the respective yeasts with YncA are given in Table 1.

From the above results, it is inferred that the above kinds of polypeptides are polypeptides having novel acyltransferase activity lower than the homology of a conventional acyltransferase, and the microorganisms including these polypeptides are also microorganisms having novel acyltransferase activity which has not been previously known.

TABLE 1

|  | Homology (%) with YncA amino acid sequence |
|---|---|
| *Pseudomonas putida*-derived acyltransferase | 65 |
| *Bacillus subtilis*-derived acyltransferase | 28 |
| *Enterobacter* sp. 638-derived acyltransferase | 82 |
| *Pseudovibrio* sp. FO-BEG1-derived acyltransferase | 46 |
| *Yarrowia lipolytica* PO1f-derived acyltransferase | 29 |
| *Corynebacterium glutamicum*-derived acyltransferase | 28 |

Example 2: Production of N-Acetylmethionine Through In Vitro Enzyme Conversion Using Novel Acyltransferase Example 2-1: Preparation of Novel Acyltransferase-Introduced *Escherichia coli*

*Pseudomonas*-derived, *Bacillus*-derived, *Enterobacter*-derived, and *Pseudovibrio*-derived novel acyltransferase genes (SEQ ID NOS. 7, 8, 9, and 10) were synthesized as codons optimized for *Escherichia coli* based on amino acid sequences (SEQ ID NOS. 1, 2, 3 and 4) of the respective enzymes.

In order to obtain a *Yarrowia*-derived novel acyltransferase gene, gDNA of *Yarrowia lipolytica* PO1f (ATCC MYA-2613™) was extracted. A gene (SEQ ID NO. 11) of a desired size and an amino acid sequence (SEQ ID NO. 5) of a desired size were obtained by performing a polymerase chain reaction using primers 1 and 2 with the gDNA as a template.

In order to obtain a *Corynebacterium*-derived novel acyltransferase gene, *Corynebacterium glutamicum* ATCC 13032 was smeared on a solid medium with streaks and then cultured overnight to obtain colonies. A gene (SEQ ID NO. 12) having a size of about 0.5 kb and an amino acid sequence (SEQ ID NO. 6) having a size of about 0.5 kb were obtained by performing PCR (polymerase chain reaction) using primers 3 and 4 with the one colony as a template. In this case, the PCR was performed by conducting denaturation at 94° C. for 5 minutes, repeating denaturation at 94° C. for 30 seconds, annealing at 56° C. for 30 seconds and polymerization at 72° C. for 1 minute 30 times, and then conducting a polymerization reaction at 72° C. for 7 minutes.

The six kinds of DNAs were treated with restriction enzymes NdeI and XbaI and then ligated to a pUCtk vector treated with the same restriction enzymes. The prepared recombinant plasmid was transformed by applying thermal shock to *Escherichia coli* DH5a at 42° C. for 90 seconds, and then those was smeared in an LB solid medium containing kanamycin and cultured overnight at 37° C. One colony obtained in the culture was inoculated in 3 mL of an LB liquid medium containing kanamycin and cultured overnight, and then the recombinant plasmid was recovered using a plasmid miniprep kit (Bioneer, Korea). Sequence information of the recovered recombinant plasmid was confirmed by sequencing (Macrogen, Korea), and the plasmids were named pUCtk-ppmat, pUCtk-bsmat, pUCtk-entmat, pUCtk-pvmat, pUCtk-ylmat, and pUCtk-cgmat.

The colonies surviving after introducing the recombinant plasmid into *Escherichia coli* BL21 (DE3) using thermal shock and smearing this in an LB solid medium containing kanamycin were selected as transformants. The selected transformants were named BL21(DE3)/pUCtk-ppmat (or *E. coli* CC03-9001), BL21(DE3)/pUCtk-bsmat (or *E. coli* CC03-9002), BL21(DE3)/pUCtk-entmat (or *E. coli* CC03-9003), BL21(DE3)/pUCtk-pvmat (or *E. coli* CC03-9004), and BL21(DE3)/pUCtk-ylmat (or *E. coli* CC03-9005), BL21(DE3)/pUCtk-cgmat (or *E. coli* CC03-9006). Further, the transformants were deposited to the Korean Culture Center of Microorganisms (KCCM) on Jul. 15, 2016 under the Budapest Treaty, and received the deposit numbers KCCM11863P, KCCM11864P, KCCM11865P, KCCM11866P, KCCM11867P, and KCCM11868P, respectively, according to the above-described order.

In order to examine the N-acetylmethionine producing capacity of the selected transformed *Escherichia coli*, one colony was inoculated in 3 mL of an LB liquid medium containing 25 mg/L of kanamycin and 0.2% (w/v) of glucose, cultured at 37° C. for 5 hours, and then further cultured for 3 hours with the addition of methionine up to 2% (w/v), so as to obtain 1 μL of a culture solution. The production of N-acetylmethionine was previously examined by thin layer chromatography (TLC) analysis using 1 μL of the culture solution. Spots presumed to be N-acetylmethionine were found in the entire culture solution, the concentration of the spots increased in the order of BL21(DE3)/pUCtk-ppmat, BL21(DE3)/pUCtk-entmat, BL21(DE3)/pUCtk-bsmat, BL21(DE3)/pUCtk-cgmat, BL21(DE3)/pUCtk-pvmat, and BL21(DE3)/pUCtk-ylmat.

TABLE 2

| Primer No. | Sequence | SEQ ID NO. |
|---|---|---|
| 1 | 5'-ATCCATATGAAGATATCTCCAGAACCC | 13 |
| 2 | 5'-TACTCTAGACTAGTCACTCCTCGTGTC | 14 |
| 3 | 5'-ATCCATATGGTTGAAAGAGACTTCAC | 15 |
| 4 | 5'-TACTCTAGATTAGGAACTTTGAGCTTG | 16 |
| 5 | 5'-ATCatgagccatgaaatt | 17 |
| 6 | 5'-GCACTGCAGtcacgccggttccgc | 18 |
| 7 | 5'-ATCatgaccctgcgcctg | 19 |
| 8 | 5'-GCACTGCAG tcagctcagttcgcg | 20 |
| 9 | 5'-ATCATGATCATCCGCCAT | 21 |
| 10 | 5'-GCACTGCAGTCAGATAGCGTCCGG | 22 |
| 11 | 5'-ATCatgaaactgcgtcag | 23 |
| 12 | 5'-GCACTGCAGttattcatgcgcgag | 24 |
| 13 | 5'-ATCATGAAGATATCTCCA | 25 |
| 14 | 5'-GCACTGCAGCTAGTCACTCCTCGT | 26 |
| 15 | 5'-ATCATGGTTGAAAGAGAC | 27 |
| 16 | 5'-GCACTGCAGTTAGGAACTTTGAGC | 28 |
| 17 | 5'-tgcactagtatgagccatgaaatt | 29 |
| 18 | 5'-tgcctcgagtcacgccggttccgc | 30 |
| 19 | 5'-tgcactagtatgaccctgcgcctg | 31 |
| 20 | 5'-tgcctcgagtcagctcagttcgcg | 32 |
| 21 | 5'-tgcactagtATGATCATCCGCCAT | 33 |
| 22 | 5'-GCACTGCAGTCAGATAGCGTCCGG | 34 |
| 23 | 5'-tgcactagtatgaaactgcgtcag | 35 |
| 24 | 5'-tgcctcgagttattcatgcgcgag | 36 |
| 25 | 5'-tgcactagtATGAAGATATCTCCA | 37 |
| 26 | 5'-tgcctcgagCTAGTCACTCCTCGT | 38 |
| 27 | 5'-tgcactagtATGGTTGAAAGAGAC | 39 |
| 28 | 5'-tgcctcgagTTAGGAACTTTGAGC | 40 |
| 29 | 5'-tgcggtaccatgagccatgaaatt | 41 |
| 30 | 5'-ctaggtacctcacgccggttccgc | 42 |
| 31 | 5'-tgcggtaccatgaccctgcgcctg | 43 |
| 32 | 5'-ctaggtacctcagctcagttcgcg | 44 |
| 33 | 5'-tgcggtaccATGATCATCCGCCAT | 45 |
| 34 | 5'-ctaggtaccTCAGATAGCGTCCGG | 46 |
| 35 | 5'-tgcggtaccatgaaactgcgtcag | 47 |
| 36 | 5'-ctaggtaccttattcatgcgcgag | 48 |

TABLE 2-continued

| Primer No. | Sequence | SEQ ID NO. |
|---|---|---|
| 37 | 5'-tgcggtaccATGAAGATATCTCCA | 49 |
| 38 | 5'-ctaggtaccCTAGTCACTCCTCGT | 50 |
| 39 | 5'-tgcggtaccATGGTTGAAAGAGAC | 51 |
| 40 | 5'-ctaggtaccTTAGGAACTTTGAGC | 52 |

Example 2-2: Confirmation of N-Acetylmethionine Production Capacity Using Novel Acyltransferase One colony of the transformed *Escherichia coli* prepared in Example 2-1 was inoculated in 3 mL of an LB liquid medium containing 25 mg/L of kanamycin and 0.2% (w/v) of glucose and cultured at 37° C. for 8 hours, and then inoculated in 50 mL of the same medium and cultured overnight, so as to obtain a culture solution. The culture solution was centrifuged to obtain pellets, the pellets were suspended in 5 mL of a 50 mM phosphate buffer (pH 7.0), and then cells were disrupted using sonication to obtain cell debris. The cell debris was removed by centrifugation at 14,000 rpm for 30 minutes to obtain a supernatant. Considering that the size of the novel acyltransferase is about 19 kDa, the filtrate was passed through an Amicon Ultra (Milipore, Ireland) 30 kDa cut-off membrane and then through a 10 kDa cut-off membrane to obtain a concentrate remaining on the filter. The concentrate filled a HiTrap Q FF column (GE, USA) filled with Q sepharose, the novel acyltransferase was purely separated using NaCl concentration gradients (80, 100, 150, 200, 300, 500 mM, in that order). The diluted enzyme was re-concentrated through an Amicon Ultra 10 kDa cut-off membrane. The degree of overexpression and purification of the novel acyltransferase was confirmed by SDS-PAGE.

In order to analyze the activity of the purified novel acyltransferase, the amount of the N-acetylmethionine produced after introducing an enzyme concentrate into a pH 7.0 phosphate buffer containing 20 mM acetyl coenzyme A and 20 mM methionine and performing a reaction at 37° C. for 10 minutes was measured using HPLC (Shimadzu, system controller CBM-20A and other accessories). Further, the concentration of the purified novel acyltransferase was measured by a Bradford assay, and then the produced N-acetylmethionine value was divided by the enzyme concentration to compare the specific activity of the enzyme (Table 3). Among the purified novel acyltransferases, the *Pseudomonas putida*-derived enzyme exhibits the highest activity of 3.8 U/mg, which is 5 times specific activity (0.745 U/mg) of YncA disclosed in the document (U.S. Pat. No. 8,143,031 B2, Table 3). In addition, the *Bacillus subtilis*-derived enzyme and the *Enterobacter* sp. 638-derived enzyme exhibit activities of 1.6 U/mg and 1.7 U/mg, respectively, each of which is 2 or more times specific activity of YncA. Each of the *Pseudovibrio* sp. FO-BEG1-derived, *Yarrowia lipolytica*-derived, and *Corynebacterium glutamicum*-derived novel acyltransferases has low specific activity of less than 1 U/mg, but the expression amount thereof on SDS-PAGE is not so small. Therefore, the N-acetylmethionine producing capacity of the transformant may be expected to be improved depending on the degree of expression in the host (Table 3).

TABLE 3

| Acyltransferase | Specific activity (U/mg) |
|---|---|
| *Pseudomonas putida*-derived | 3.8 |
| *Bacillus subtilis*-derived | 1.6 |
| *Enterobacter* sp. 638-derived | 1.7 |
| *Pseudovibrio* sp. FO-BEG1-derived | 0.4 |
| *Yarrowia lipolytica* PO1f-derived | 0.4 |
| *Corynebacterium glutamicum*-derived | 0.8 |

Example 3: N-Acetylmethionine Conversion Reaction Using *Pseudomonas putida*-Derived Novel Acyltransferase

Example 3-1: N-Acetylmethionine Conversion Reaction Using *Pseudomonas putida*-Derived Purified Novel Acyltransferase A methionine conversion reaction was performed using 1 mg of the *Pseudomonas putida*-derived purified acyltransferase, which had the highest activity in Example 2. 3 ml of a 50 mM phosphate buffer of pH 7.0 containing 20 mM methionine and 20 mM acetyl coenzyme A was used as a substrate solution. When the reaction solution was analyzed by HPLC (SHIMADZU, SYSTEM CONTROLLER CBM-20A and other accessories) after reaction for 3 hours under conditions of 37° C. and 150 rpm, the production of 3.1 g/L of N-acetylmethionine was confirmed. This is a value obtained by converting methionine and acetyl coenzyme A in the reaction solution by 75% or more.

Example 3-2: N-Acetylmethionine Conversion Reaction of Cell Provided Therein with *Pseudomonas putida*-Derived Acyltransferase Depending on Increase of Cell Membrane Permeability One colony of the transformed *Escherichia coli* BL21 (DE3)/pUCtk-ppmat made by introducing the *Pseudomonas putida*-derived novel acyltransferase gene prepared in Example 2 was inoculated in 3 ml of an LB liquid medium containing 25 mg/L of kanamycin and 1% (w/v) of glucose and cultured at 37° C. for 8 hours to obtain a culture solution, and then 50 μL of the culture solution was inoculated in 50 mL of an LB liquid medium containing 25 mg/L of kanamycin and 0.2% (w/v) of glucose and cultured overnight. The culture solution was centrifuged to obtain cell pellets, the cell pellets were frozen in a refrigerator at −20° C. The processes of remelting the fully frozen cell pellets at room temperature and refreezing these cell pellets were repeated three times to impart high permeability to the cell membrane. The culture solution was resuspended to a total volume of 5 mL by adding a 50 mM phosphate buffer (pH 7.0) to concentrate the culture solution. 1.8 mL of a 50 mM phosphate buffer (pH 7.0) containing 2% (w/v) methionine; 1.8 mL of a 50 mM phosphate buffer (pH 7.0) containing 2% (w/v) methionine and 20 mM acetyl coenzyme A; and 1.8 mL of a 50 mM phosphate buffer (pH 7.0) containing 2% (w/v) methionine and 2% (w/v) glucose were respectively put into 15 mL test tubes, and were each mixed with the enzyme bacteria having improved cell membrane permeability obtained through the above procedures by 200 μL to a total volume of 2 mL, and were then reacted for 10 hours under conditions of 37° C. and 150 rpm. The purpose of adding glucose to the reaction solution is to increase the production amount of acetyl coenzyme A, which may be deficient in the reaction, and is not intended for the survival of *Escherichia coli*. The reaction solution was analyzed by HPLC (SHIMADZU, SYSTEM CONTROLLER CBM-20A and other accessories), and the results thereof are given in Table 4. As given in Table 4, it was found that when the acetyl coenzyme A was added at the time of fermentation, the molar conversion rate of the reaction solution was increased compared to when the acetyl coenzyme A was not added. Further, since it was found that the molar conversion rate of the reaction solution was increased even when sucrose was added instead of the acetyl coenzyme A, it was estimated that the addition of glucose makes a portion of the acetyl coenzyme A. As the result of using strains each having a high-permeability cell membrane, N-acetylmethionine was able to be produced at high concentration, and was also able to be produced at high concentration even when only glucose was added to the medium instead of the acetyl coenzyme A.

TABLE 4

| Addition in reaction solution | N-Acetylmethionine concentration (g/L) | Molar conversion rate (%) |
|---|---|---|
| Not added | 13.1 | 51 |
| Acetyl coenzyme A | 20.0 | 78 |
| Glucose | 18.7 | 73 |

Example 4: Production of N-Acetyl-L-Methionine Through Fermentation of Transformant Provided Therein with Novel Acyltransferase Example 4-1: Production of N-Acetyl-L-Methionine Through *Escherichia coli* Provided Therein with Novel Acyltransferase One of the colonies of the six kinds of transformants prepared in Example 2 was inoculated in 3 mL of an LB liquid medium containing 25 mg/L of kanamycin and 1% (w/v) of glucose and cultured at 37° C. for 8 hours to obtain a culture solution, and then the culture solution was inoculated in 50 mL of an LB liquid medium containing 25 mg/L of kanamycin, 0.2% (w/v) of glucose, and 2% (w/v) of methionine and cultured overnight. In this case, as a control group, a pUCtk empty vector was transformed into BL21 (DE3) and used. After the cells in the culture solution were removed by centrifugation, the produced N-acetylmethionine was analyzed using HPLC (SHIMADZU, SYSTEM CONTROLLER CBM-20A and other accessories). In the case of BL21(DE3)/pUCtk-ppmat, N-acetylmethionine was produced at the highest concentration of 3.03 g/L. In the case of BL21(DE3)/pUCtk-entmat, N-acetylmethionine was produced at the second highest concentration of 2.23 g/L. Even in the case of the empty vector, a trace amount of N-acetylmethionine was detected, which is presumed to be a role of the YncA enzyme possessed by *Escherichia coli* (Table 5).

TABLE 5

| Transformant | Concentration of N-acetylmethionine in culture solution (g/L) |
|---|---|
| BL21(DE3)/pUCtk | <0.1 |
| BL21(DE3)/pUCtk-ppmat | 3.03 |
| BL21(DE3)/pUCtk-bsmat | 1.60 |

TABLE 5-continued

| Transformant | Concentration of N-acetylmethionine in culture solution (g/L) |
|---|---|
| BL21(DE3)/pUCtk-entmat | 2.23 |
| BL21(DE3)/pUCtk-pvmat | 0.17 |
| BL21(DE3)/pUCtk-ylmat | 0.13 |
| BL21(DE3)/pUCtk-cgmat | 0.58 |

Example 4-2: Production of N-Acetyl-L-Methionine Through *Corynebacterium* Provided Therein with Novel Acyltransferase Example 4-2-1: Preparation of Acyltransferase Overexpression Vector for Introducing Microorganism of Genus *Corynebacterium*

In order to examine the effect of N-acetyl-L-methionine production of the novel acyltransferases (SEQ ID NOS. 1, 2, 3, 4, 5, and 6) confirmed from Example 1 in microorganisms of genus *Corynebacterium*, vectors for overexpressing the corresponding genes were prepared. A primer in which an EcoRV restriction enzyme site is inserted at the 5' end and a primer in which a PstI site is inserted at the 3' end were synthesized based on base sequences 7, 8, 9, 10, 11, and 12.

The gene based on base sequence 7 was polymerized through PCR using the vector pUCtk-ppmat of Example 1 as a template and using primers 5 and 6. The gene based on base sequence 8 was polymerized through PCR using the vector pUCtk-bsmat of Example 1 as a template and using primers 7 and 8. The gene based on base sequence 9 was polymerized through PCR using the vector pUCtk-entmat of Example 1 as a template and using primers 9 and 10. The gene based on base sequence 10 was polymerized through PCR using the vector pUCtk-pvmat of Example 1 as a template and using primers 11 and 12. The gene based on base sequence 11 was polymerized through PCR using the vector pUCtk-ylmat of Example 1 as a template and using primers 13 and 14. The gene based on base sequence 12 was polymerized through PCR using the vector pUCtk-cgmat of Example 1 as a template and using primers 15 and 16.

As the promoter of the acyltransferase, a promoter cj7 (Korean Unexamined Patent Application Publication No. 10-2004-0107215) was used. In order to obtain the DNA fragment of the cj7 promoter, a primer in which a KpnI restriction enzyme is inserted at the 5' end and a primer in which an EcoRV site is inserted at the 3' end were synthesized, and the cj7 promoter was amplified through PCR using p117-cj1-gfp as a template (Korean Patent Application Publication No. 10-2004-0107215). In this case, PCR was performed by conducting denaturation at 94° C. for 5 minutes, repeating denaturation at 94° C. for 30 seconds, annealing at 56° C. for 30 seconds and polymerization at 72° C. for 1 minute 30 times, and then conducting a polymerization reaction at 72° C. for 7 minutes.

The six kinds of amplified acyltransferase polynucleotides were treated with restriction enzyme PstI to obtain DNA fragments, and the cj7 promoter polynucleotide was treated with KpnI and EcoRV to obtain a DNA fragment. After six DNA fragments were obtained, they were linked to the KpnI and PstI sites of the pECCG117 vector, which is a shuttle vector of *Escherichia* and *Corynebacterium*, to be transformed into *Escherichia coli* DH5α, and were smeared in an LB solid medium containing kanamycin (25 mg/L). The colonies transformed with the vector into which the gene was inserted were selected by PCR, and then plasmids were obtained using a generally known plasmid extraction method. The obtained plasmids were named pECCG117-Pcj7-ppmat, pECCG117-Pcj7-bsmat, pECCG117-Pcj7-entmat, pECCG117-Pcj7-pvmat, pECCG117-Pcj7-ylmat, and pECCG117-Pcj7-cgmat.

Example 4-2-2: Preparation of Strain for Introducing Novel Acyltransferase Overexpression Vector and Confirmation of N-Acetyl-L-Methionine Production Capacity Each of the vectors pECCG117-Pcj7-ppmat, pECCG117-Pcj7-bsmat, pECCG117-Pcj7-entmat, pECCG117-Pcj7-pvmat, pECCG117-Pcj7-ylmat, and pECCG117-Pcj7-cgmat, prepared in Example 4-2-1, and vector pECCG117 of the experimental control group was introduced into the *Corynebacterium glutamicum* ATCC13032 using an electric pulse method, smeared in a composite plate medium containing kanamycin (25 mg/L), and then cultured at 30° C. for 24 hours to obtain strains. The obtained strains were named 13032/pECCG117-Pcj7-ppmat, 13032/pECCG117-Pcj7-bsmat, 13032/pECCG117-Pcj7-entmat, 13032/pECCG117-Pcj7-pvmat, 13032/pECCG117-Pcj7-ylmat, 13032/pECCG117-Pcj7-cgmat, and 13032/pECCG117. In order to confirm the N-acetylmethionine production capacity of the transformant, the strains were inoculated in 14 mL of a disposable culture tube including 3 mL of a composite liquid medium containing kanamycin (25 mg/L), and shake-cultured for 24 hours under conditions of 30° C. and 200 rpm to obtain a seed culture solution. 1 mL of the seed culture solution was inoculated in a 250 mL corner-baffle flask including 24 mL of a composite liquid medium containing kanamycin (25 mg/L) and methionine (2% (20 g/L)), and shake-cultured for 24 hours under conditions of 37° C. and 200 rpm. After completing the culture, the concentration of N-acetylmethionine was analyzed using HPLC (SHIMADZU, SYSTEM CONTROLLER CBM-20A and other accessories) (Table 6).

In the case of the transformant 13032/pECCG117 prepared as a control group, 1.07 g/L of N-acetylmethionine was produced. This result is presumed to be caused by the ability of the acyltransferase possessed by *Corynebacterium glutamicum*, which is a parent strain. Further, it can be ascertained that a larger amount of N-acetylmethionine is produced as compared with original ability as the result of overexpressing the six kinds of novel acyltransferases.

<Composite Plate Medium>
20 g glucose, 50 g $(NH_4)_2SO_4$, 10 g peptone, 5 g yeast extract, 1.5 g urea, 5 g $KH_2PO_4$, 10 g $K_2HPO_4$, 0.5 g $MgSO_4 7H_2O$, 100 μg biotin, 1000 μg thiamine HCl, 2000 μg calcium pantothenate, 2000 μg nicotinamide, 20 g agar, and 25 mg kanamycin (based on 1 L distilled water)

<Composite Liquid Medium>
20 g glucose, 10 g peptone, 5 g yeast extract, 1.5 g urea, 4 g $KH_2PO_4$, 8 g $K_2HPO_4$, 0.5 g $MgSO_4 7H_2O$, 100 μg biotin, 1000 μg thiamine HCl, 2000 μg calcium pantothenate, 2000 μg nicotinamide, and 25 mg kanamycin (based on 1 L distilled water)

TABLE 6

| Transformant | Concentration of N-acetylmethionine in culture solution (g/L) |
|---|---|
| 13032/pECCG117 | 1.07 |
| 13032/pECCG117-Pcj7-ppmat | 2.50 |
| 13032/pECCG117-Pcj7-bsmat | 1.79 |

TABLE 6-continued

| Transformant | Concentration of N-acetylmethionine in culture solution (g/L) |
|---|---|
| 13032/pECCG117-Pcj7-entmat | 2.11 |
| 13032/pECCG117-Pcj7-pvmat | 1.23 |
| 13032/pECCG117-Pcj7-ylmat | 1.31 |
| 13032/pECCG117-Pcj7-cgmat | 2.58 |

Example 4-3: Production of N-Acetyl-L-Methionine Through *Saccharomyces* Provided Therein with Novel Acyltransferase

Example 4-3-1: Preparation of Acyltransferase Overexpression Vector for *Saccharomyces*

In order to examine the effect of N-acetyl-L-methionine production of the novel acyltransferases (SEQ ID NOS. 1, 2, 3, 4, 5, and 6) confirmed from Example 1 in *Saccharomyces*, vectors for overexpressing the corresponding genes were prepared. A primer in which a SpeI restriction enzyme site is inserted at the 5' end and a primer in which a XhoI site is inserted at the 3' end were synthesized based on base sequences 7, 8, 9, 10, 11, and 12.

The gene based on base sequence 7 was polymerized through PCR using the vector pUCtk-ppmat of Example 1 as a template and using primers 17 and 18. The gene based on base sequence 8 was polymerized through PCR using the vector pUCtk-bsmat of Example 1 as a template and using primers 19 and 20. The gene based on base sequence 9 was polymerized through PCR using the vector pUCtk-entmat of Example 1 as a template and using primers 21 and 22. The gene based on base sequence 10 was polymerized through PCR using the vector pUCtk-pvmat of Example 1 as a template and using primers 23 and 24. The gene based on base sequence 11 was polymerized through PCR using the vector pUCtk-ylmat of Example 1 as a template and using primers 25 and 26. The gene based on base sequence 12 was polymerized through PCR using the vector pUCtk-cgmat of Example 1 as a template and using primers 27 and 28. In this case, the PCR was performed by conducting denaturation at 94° C. for 5 minutes, repeating denaturation at 94° C. for 30 seconds, annealing at 56° C. for 30 seconds and polymerization at 72° C. for 1 minute 30 times, and then conducting a polymerization reaction at 72° C. for 7 minutes.

The six kinds of amplified acyltransferase polynucleotides were treated with restriction enzymes SpeI and XhoI to obtain DNA fragments. After six DNA fragments were obtained, they are linked to the SpeI and XhoI sites of the p414ADH vector, which is a shuttle vector of *Escherichia* and *Saccharomyces*, to be transformed into *Escherichia coli* DH5a, and were smeared in an LB solid medium containing ampicillin (100 mg/L). The colonies transformed with the vector into which the gene was inserted were selected by PCR, and then plasmids were obtained using a plasmid miniprep kit (Bioneer, Korea). The obtained plasmids were named p414ADH-ppmat, p414ADH-bsmat, p414ADH-entmat, p414ADH-pvmat, p414ADH-ylmat, and p414ADH-cgmat.

Example 4-3-2: Preparation of Strain for Introducing Novel Acyltransferase Overexpression Vector and Confirmation of N-Acetyl-L-Methionine Production Capacity Each of the vectors p414ADH-ppmat, p414ADH-bsmat, p414ADH-entmat, p414ADH-pvmat, p414ADH-ylmat, and p414ADH-cgmat, prepared in Example 4-3-1, and vector pECCG117 of the experimental control group was introduced into *Saccharomyces cerevisiae* CEN.PK2-1D (Korean Patent Registration No. 10-1577134), which is a typical wild yeast received from EUROSCARF, using a yeast transformation method. The vectors were introduced into the *Saccharomyces cerevisiae* CEN.PK2-1D, and then smeared in a YPD plate medium (1% yeast extract, 2% bacto-peptone, 2% glucose), and cultured at 30° C. for 24 hours to obtain strains. The obtained strains were named ScCEN/p414ADH-ppmat, ScCEN/p414ADH-bsmat, ScCEN/p414ADH-entmat, ScCEN/p414ADH-pvmat, ScCEN/p414ADH-ylmat, ScCEN/p414ADH-cgmat, and ScCEN/p414ADH. In order to confirm the N-acetylmethionine production capacity of the transformant, the strains were inoculated in 14 mL of a disposable culture tube including 3 mL of a YPD liquid medium containing ampicillin (100 mg/L), and shake-cultured for 24 hours under conditions of 30° C. and 200 rpm to obtain a seed culture solution. 1 mL of the seed culture solution was inoculated in a 250 mL corner-baffle flask including 24 mL of a YPD liquid medium containing methionine (0.5% (5 g/L)), and shake-cultured for 24 hours under conditions of 30° C. and 200 rpm. After completing the culturing, the concentration of N-acetyl-L-methionine was analyzed using HPLC (SHIMADZU, SYSTEM CONTROLLER CBM-20A and other accessories) (Table 7).

In the case of the transformant 13032/pECCG117 prepared as a control group, 1.07 g/L of N-acetylmethionine was produced. This result is presumed to be caused by the ability of the acyltransferase possessed by *Corynebacterium glutamicum*, which is a parent strain. Further, it can be ascertained that a larger amount of N-acetylmethionine is produced as compared with the original ability as a result of overexpressing the six kinds of novel acyltransferases.

As can be seen from the transformant ScCEN/p414ADH, it is presumed that *Saccharomyces cerevisiae* itself does not produce N-acetylmethionine, but it was ascertained that the strains in which six kinds of novel acyltransferases are overexpressed have N-acetylmethionine production capacity.

TABLE 7

| Transformant | Concentration of N-acetylmethionine in culture solution (g/L) |
| --- | --- |
| ScCEN/p414ADH | 0 |
| ScCEN/p414ADH-ppmat | 1.64 |
| ScCEN/p414ADH-bsmat | 1.44 |
| ScCEN/p414ADH-entmat | 1.65 |
| ScCEN/p414ADH-pvmat | 0.42 |
| ScCEN/p414ADH-ylmat | 1.40 |
| ScCEN/p414ADH-cgmat | 0.30 |

Example 4-4: Production of N-Acetyl-L-Methionine Through *Yarrowia* Provided Therein with Novel Acyltransferase Example 4-4-1: Preparation of Acyltransferase Overexpression Vector for *Yarrowia*

In order to examine the effect of N-acetyl-L-methionine production of the novel acyltransferases (SEQ ID NOS. 1, 2, 3, 4, 5, and 6) confirmed from Example 1 in *Yarrowia*, vectors for overexpressing the corresponding genes were prepared. A primer in which a KpnI restriction enzyme site is inserted at the 5' end and a primer in which a KpnI restriction enzyme site is inserted at the 3' end were synthesized based on base sequences 7, 8, 9, 10, 11, and 12.

The gene based on base sequence 7 was polymerized through PCR using the vector pUCtk-ppmat of Example 1 as a template and using primers 29 and 30. The gene based on base sequence 8 was polymerized through PCR using the vector pUCtk-bsmat of Example 1 as a template and using primers 31 and 32. The gene based on base sequence 9 was polymerized through PCR using the vector pUCtk-entmat of Example 1 as a template and using primers 33 and 34. The gene based on base sequence 10 was polymerized through PCR using the vector pUCtk-pvmat of Example 1 as a template and using primers 35 and 36. The gene based on base sequence 11 was polymerized through PCR using the vector pUCtk-ylmat of Example 1 as a template and using primers 37 and 38. The gene based on base sequence 12 was polymerized through PCR using the vector pUCtk-cgmat of Example 1 as a template and using primers 39 and 40. In this case, the PCR was performed by conducting denaturation at 94° C. for 5 minutes, repeating denaturation at 94° C. for 30 seconds, annealing at 56° C. for 30 seconds and polymerization at 72° C. for 1 minute 30 times, and then conducting a polymerization reaction at 72° C. for 7 minutes.

The six kinds of amplified acyltransferase polynucleotides were treated with restriction enzyme KpnI to obtain DNA fragments. After six DNA fragments were obtained, they are linked to the KpnI site of a shuttle vector pIMR53_AUX (FEMS Microbiology LettersVolume 199, Issue 1, pages 97-102, May 2001) of *Escherichia* and *Yarrowia*, to be transformed into *Escherichia coli* DH5α, and were smeared in an LB solid medium containing ampicillin (100 mg/L). The colonies transformed with the vector into which the gene was inserted were selected by PCR, and then plasmids were obtained using a plasmid miniprep kit (Bioneer, Korea). The obtained plasmids were named pIMR53U-ppmat, pIMR53U-bsmat, pIMR53U-entmat, pIMR53U-pvmat, pIMR53U-ylmat, and pIMR53U-cgmat.

Example 4-4-2: Preparation of Strain for Introducing Acyltransferase Overexpression Vector and Confirmation of N-Acetyl-L-Methionine Production Capacity Each of the vectors pIMR53U-ppmat, pIMR53U-bsmat, pIMR53U-entmat, pIMR53U-pvmat, pIMR53U-ylmat, and pIMR53U-cgmat, and vector pIMR53_AUX of the experimental control group was introduced into *Yarrowia lipolytica* PO1f (ATCC MYA-2613™) purchased from American type Culture Collection using a yeast transformation method. The vectors were introduced into the *Yarrowia lipolytica* PO1f, and then smeared in a YPD plate medium (1% yeast extract, 2% bacto-peptone, 2% glucose), and cultured at 30° C. for 24 hours to obtain strains. The obtained strains were named Yl/pIMR53U-ppmat, Yl/pIMR53U-bsmat, Yl/pIMR53U-entmat, Yl/pIMR53U-pvmat, Yl/pIMR53U-ylmat, Yl/pIMR53U-cgmat, and Yl/pIMR53U. In order to confirm the N-acetylmethionine production capacity of the transformant, the strains were inoculated in 14 mL of a disposable culture tube including 3 mL of a YPD liquid medium, and shake-cultured for 24 hours under conditions of 30° C. and 200 rpm to obtain a seed culture solution. 1 mL of the seed culture solution was inoculated in a 250 mL corner-baffle flask including 24 mL of a YPDm liquid medium (10 g glucose, 3.28 g $Na_2HPO_4$, 3.22 g $NaH_2PO_4$, 2 g yeast extract, and 50 g/L Proteose-peptone) containing methionine (0.5% (5 g/L)), and shake-cultured for 24 hours under conditions of 30° C. and 200 rpm. After completing the culturing, the concentration of N-acetyl-L-methionine was analyzed using HPLC (SHIMADZU, SYSTEM CONTROLLER CBM-20A and other accessories) (Table 8).

It is presumed that N-acetylmethionine is also produced in the transformant Y/pIMR53U due to the effect of the acyltransferase possessed by the wild type of *Yarrowia lipolytica*, but it was ascertained that the strains in which six kinds of novel acyltransferases are overexpressed have N-acetylmethionine production capacity.

TABLE 8

| Transformant | Concentration of N-acetyl-L-methionine in culture solution (g/L) |
|---|---|
| YI/pIMR53U | 1.02 |
| YI/pIMR53U-ppmat | 1.92 |
| YI/pIMR53U-bsmat | 1.78 |
| YI/pIMR53U-entmat | 1.82 |
| YI/pIMR53U-pvmat | 1.26 |
| YI/pIMR53U-ylmat | 2.01 |
| YI/pIMR53U-cgmat | 1.38 |

From the above results, it is suggested that acyltransferases newly developed in the present disclosure and microorganisms including the same efficiently produce N-acetyl-L-methionine as compared with a known acyltransferase YncA.

As described above, those skilled in the art will be able to understand that the present disclosure can be easily executed in other detailed forms without changing the technical spirit or an essential feature thereof. Therefore, it should be appreciated that the aforementioned embodiments are illustrative in all aspects and are not restricted. The scope of the present disclosure is represented by claims to be described below rather than the detailed description, and it is to be interpreted that the meaning and scope of the claims and all changes or modified forms derived from the equivalents thereof come within the scope of the present disclosure.

The invention claimed is:

1. A method of preparing N-acetyl-L-methionine, comprising:
   acetylating L-methionine using (A) a microorganism producing N-acetyl-L-methionine from L-methionine, the microorganism comprising a polypeptide having an acyltransferase activity and having (i) an amino acid sequence identical to any one of SEQ ID NOS. 1-3 or (ii) an amino acid sequence having 90% or more homology to one of such amino acid sequences or (B) a culture of the microorganism,
   wherein the microorganism is selected from the group consisting of an *Escherichia* sp., *Corynebacterium* sp., *Saccharomyces* sp., and *Yarrowias* p.

2. The method according to claim 1, further comprising: recovering N-acetyl-L-methionine, which is the acetylated L-methionine.

3. A method of preparing N-acetyl-L-methionine, comprising: acetylating L-methionine using (A) a microorganism producing N-acetyl-L-methionine from L-methionine, the microorganism comprising a polypeptide having an acyltransferase activity and having (i) an amino acid sequence identical to any one of SEQ ID NOS. 1-3 or (ii) an amino acid sequence having 90% or more homology to one of such amino acid sequences or (B) a culture of the microorganism, wherein the microorganism is an *Escherichia* sp.

4. The method of claim 3, comprising: acetylating L-methionine using (A) a microorganism producing N-acetyl-L-methionine from L-methionine, the microorganism comprising a polypeptide having an acyltransferase activity and having an amino acid sequence identical to any one of SEQ ID NOS. 1-3 or (B) a culture of the microorganism, wherein the microorganism is an *Escherichia* sp.

5. The method according to claim 4, further comprising recovering N-acetyl-L-methionine, which is the acetylated L-methionine.

* * * * *

SEQUENCE LISTING

<160> NUMBER OF SEQ ID NOS: 52

<210> SEQ ID NO 1
<211> LENGTH: 171
<212> TYPE: PRT
<213> ORGANISM: Pseudomonas putida

<400> SEQUENCE: 1

Met Ser His Glu Ile Arg Asp Ala Leu Pro Ala Asp Val Pro Gly Ile
1               5                   10                  15

Leu Asp Ile Tyr Asn Asp Ala Val Arg Asn Thr Thr Ala Ile Trp Asn
                20                  25                  30

Glu Thr Pro Val Asp Leu Gly Asn Arg Gln Ala Trp Phe Glu Ala Arg
            35                  40                  45

Ala Gln Gln Gly Tyr Pro Ile Leu Val Ala Val Asp His Ser Gly Val
        50                  55                  60

Leu Gly Tyr Ala Ser Phe Gly Asp Trp Arg Pro Phe Glu Gly Phe Arg
65                  70                  75                  80

Asn Thr Val Glu His Ser Val Tyr Ile Arg Gly Asp Gln Arg Gly Lys
                85                  90                  95

Gly Leu Gly Pro Gln Leu Met Thr Ala Leu Ile Ala Arg Ala Arg Gly
            100                 105                 110

Cys Gly Lys His Val Met Val Ala Ala Ile Glu Ser Gly Asn Ala Ala
        115                 120                 125

Ser Val Arg Leu His Glu Arg Leu Gly Phe Val Val Thr Gly Gln Met
    130                 135                 140

Pro Gln Val Gly Val Lys Phe Gly Arg Trp Leu Asp Leu Thr Phe Met
145                 150                 155                 160

Gln Leu Val Leu Asp Pro Gly Ala Glu Pro Ala
                165                 170

<210> SEQ ID NO 2
<211> LENGTH: 163
<212> TYPE: PRT
<213> ORGANISM: Bacillus subtilis

<400> SEQUENCE: 2

```
Met Thr Leu Arg Leu Ala Glu His Arg Asp Leu Glu Ala Val Val Ala
1               5                   10                  15

Ile Tyr Asn Ser Thr Ile Ala Ser Arg Met Val Thr Ala Asp Thr Glu
            20                  25                  30

Pro Val Thr Pro Glu Asp Arg Met Glu Trp Phe Ser Gly His Thr Glu
        35                  40                  45

Ser Arg Pro Leu Tyr Val Ala Glu Asp Glu Asn Gly Asn Val Ala Ala
    50                  55                  60

Trp Ile Ser Phe Glu Thr Phe Tyr Gly Arg Pro Ala Tyr Asn Lys Thr
65                  70                  75                  80

Ala Glu Val Ser Ile Tyr Ile Asp Glu Ala Cys Arg Gly Lys Gly Val
                85                  90                  95

Gly Ser Tyr Leu Leu Gln Glu Ala Leu Arg Ile Ala Pro Asn Leu Gly
            100                 105                 110

Ile Arg Ser Leu Met Ala Phe Ile Phe Gly His Asn Lys Pro Ser Leu
        115                 120                 125

Lys Leu Phe Glu Lys His Gly Phe Ala Glu Trp Gly Leu Phe Pro Gly
    130                 135                 140

Ile Ala Glu Met Asp Gly Lys Arg Tyr Asp Leu Lys Ile Leu Gly Arg
145                 150                 155                 160

Glu Leu Ser
```

<210> SEQ ID NO 3
<211> LENGTH: 171
<212> TYPE: PRT
<213> ORGANISM: Enterobacter sp. 638

<400> SEQUENCE: 3

```
Met Ile Ile Arg His Ala Ser Lys Glu Asp Cys Ala Ala Ile Gly Glu
1               5                   10                  15

Ile Tyr Asn His Ala Val Val His Thr Ala Ala Ile Trp Asn Asp Thr
            20                  25                  30

Thr Val Asp Thr Glu Asn Arg Ile Ala Trp Phe Glu Ala Arg Thr Leu
        35                  40                  45

Met Gly Tyr Pro Val Leu Val Ser Glu Glu Asn Gly Val Val Thr Gly
    50                  55                  60

Tyr Ala Ser Phe Gly Asp Trp Arg Ala Phe Asp Gly Phe Arg His Thr
65                  70                  75                  80

Val Glu His Ser Val Tyr Val His Pro Asp His Gln Gly Lys Gly Ile
                85                  90                  95

Gly Arg Glu Leu Met Lys Ala Leu Ile Gly Glu Ala Arg Asn Ile Gly
            100                 105                 110

Lys His Val Met Val Ala Gly Ile Glu Ala Gln Asn His Gly Ser Ile
        115                 120                 125

His Leu His Lys Thr Leu Gly Phe Val Ile Thr Gly Gln Met Pro Gln
    130                 135                 140

Val Gly Thr Lys Phe Gly Arg Trp Leu Asp Leu Thr Phe Met Gln Leu
145                 150                 155                 160

Gln Leu Asp Glu Arg Ile Asp Pro Asp Ala Ile
                165                 170
```

<210> SEQ ID NO 4
<211> LENGTH: 175
<212> TYPE: PRT

<213> ORGANISM: Pseudovibrio sp. FO-BEG1

<400> SEQUENCE: 4

Met Lys Leu Arg Gln Ala Thr Lys Ser Asp Leu Pro Thr Leu Leu Glu
1               5                   10                  15
Ile His Asn Asp Ala Val Lys Thr Leu Ala Ala Ile Trp Thr Asp Thr
            20                  25                  30
Leu Glu Thr Leu Glu Asp Arg Val Ser Trp Phe Glu Lys Arg Ile Ala
        35                  40                  45
Gly Gly Phe Pro Ile Ile Val Ala Glu Asp Glu Asn Gly Asp Val Leu
    50                  55                  60
Gly Tyr Gly Ser Tyr Gly Ser Phe Arg Glu Lys Ser Gly Tyr Asp Lys
65                  70                  75                  80
Thr Val Glu His Ser Val Tyr Val Thr Pro Gln Ser Arg Gly Asn Gly
                85                  90                  95
Ala Gly Ser Val Leu Leu Glu Lys Leu Ile Glu Leu Ala Lys Gln Asp
            100                 105                 110
Asp Arg His Val Leu Ile Gly Ala Ile Asp Ser Glu Asn Lys Gly Ser
        115                 120                 125
Ile Arg Leu His Glu Arg Tyr Gly Phe Arg Ile Thr Gly Glu Leu Pro
    130                 135                 140
Gln Val Gly Phe Lys Phe Gly Arg Trp Leu Asp Leu Thr Leu Met Thr
145                 150                 155                 160
Leu Ile Leu Asn Asp Asp Glu Ala Pro Thr Ala Leu Ala His Glu
                165                 170                 175

<210> SEQ ID NO 5
<211> LENGTH: 154
<212> TYPE: PRT
<213> ORGANISM: Yarrowia lipolytica PO1f

<400> SEQUENCE: 5

Met Lys Ile Ser Pro Glu Pro Tyr Thr Ala Asp Leu Tyr Lys Leu Val
1               5                   10                  15
Arg Lys Asn Met Lys Gly Met Tyr Glu Gly Ser Gly Met Gly Trp Asn
            20                  25                  30
Arg Val Asp Lys Ile Asp Glu Met Glu Asp Glu Leu Ala Tyr His
        35                  40                  45
Val Ala Arg Glu Asn Gly Glu Met Leu Gly Phe Val Ser Phe Met His
    50                  55                  60
Thr Val Glu Asp Val Glu Val Val Tyr Leu Tyr Glu Leu Gln Val
65                  70                  75                  80
Ala Lys Gly Arg Gln Gly His Gly Val Gly Lys Glu Leu Met Arg Val
                85                  90                  95
Val Ile Asp Glu Ala Arg Ala Cys Gly Arg Pro Ile Met Leu Thr Val
            100                 105                 110
Phe Leu Met Asn Glu Arg Ala Ile Gly Phe Tyr Arg Arg Tyr Gly Phe
        115                 120                 125
Glu Arg Val Gly Arg Gly Pro Gln Glu Gly Lys Arg Val Arg Gly Trp
    130                 135                 140
Met Gln Met Arg Arg Asp Thr Arg Ser Asp
145                 150

<210> SEQ ID NO 6
<211> LENGTH: 179
<212> TYPE: PRT

<213> ORGANISM: Corynebacterium glutamicum ATCC 13032

<400> SEQUENCE: 6

| Met | Val | Glu | Arg | Asp | Phe | Thr | Ile | Arg | Pro | Ile | Arg | Glu | Gly | Asp | Phe |
|---|---|---|---|---|---|---|---|---|---|---|---|---|---|---|---|
| 1 | | | | 5 | | | | | 10 | | | | | 15 | |

| Pro | Gln | Val | Arg | Asp | Ile | Tyr | Glu | Leu | Gly | Leu | Glu | Thr | Gly | His | Ala |
|---|---|---|---|---|---|---|---|---|---|---|---|---|---|---|---|
| | | | 20 | | | | | 25 | | | | | 30 | | |

| Thr | Tyr | Glu | Thr | Ser | Gly | Pro | Thr | Trp | Asp | Gln | Phe | Ser | Gln | Ser | Lys |
|---|---|---|---|---|---|---|---|---|---|---|---|---|---|---|---|
| | | 35 | | | | | 40 | | | | | 45 | | | |

| Ile | Met | Asp | Thr | Val | Met | Val | Ala | Val | Glu | Asn | Asn | Asp | Pro | Asp | Phe |
|---|---|---|---|---|---|---|---|---|---|---|---|---|---|---|---|
| | 50 | | | | | 55 | | | | | 60 | | | | |

| Ile | Leu | Gly | Trp | Val | Ser | Ala | Ala | Pro | Ile | Ser | Ser | Arg | Gln | Val | Phe |
|---|---|---|---|---|---|---|---|---|---|---|---|---|---|---|---|
| 65 | | | | | 70 | | | | | 75 | | | | | 80 |

| His | Gly | Val | Val | Glu | Asp | Ser | Ile | Tyr | Ile | His | Pro | Gln | Gly | Gln | Gly |
|---|---|---|---|---|---|---|---|---|---|---|---|---|---|---|---|
| | | | | 85 | | | | | 90 | | | | | 95 | |

| Arg | Gly | Ile | Gly | Gly | Ala | Leu | Leu | Asp | Ala | Leu | Ile | Thr | Tyr | Cys | Glu |
|---|---|---|---|---|---|---|---|---|---|---|---|---|---|---|---|
| | | | 100 | | | | | 105 | | | | | 110 | | |

| Ser | Asn | Gly | Ile | Trp | Ser | Ile | His | Ser | Trp | Ile | Phe | Pro | Glu | Asn | Leu |
|---|---|---|---|---|---|---|---|---|---|---|---|---|---|---|---|
| | | 115 | | | | | 120 | | | | | 125 | | | |

| Gly | Ser | Ala | Lys | Leu | His | Glu | Ser | Lys | Gly | Phe | Val | Lys | Val | Gly | Thr |
|---|---|---|---|---|---|---|---|---|---|---|---|---|---|---|---|
| | 130 | | | | | 135 | | | | | 140 | | | | |

| Met | His | Gln | Met | Ala | Arg | Met | Pro | Tyr | Gly | Glu | Met | Glu | Gly | Gln | Trp |
|---|---|---|---|---|---|---|---|---|---|---|---|---|---|---|---|
| 145 | | | | | 150 | | | | | 155 | | | | | 160 |

| Arg | Asp | Cys | Asp | Leu | Trp | Glu | Cys | Leu | Leu | Ser | Val | Pro | Glu | Gln | Ala |
|---|---|---|---|---|---|---|---|---|---|---|---|---|---|---|---|
| | | | | 165 | | | | | 170 | | | | | 175 | |

Gln Ser Ser

<210> SEQ ID NO 7
<211> LENGTH: 516
<212> TYPE: DNA
<213> ORGANISM: Pseudomonas putida

<400> SEQUENCE: 7

```
atgagccatg aaattcgcga tgcgctgccg gcggatgtgc cgggcattct ggatatttat     60
aacgatgcgg tgcgcaacac cacggcgatt tggaacgaaa ccccggtgga tctgggcaac    120
cgccaggcgt ggtttgaagc gcgcgcgcag cagggctatc cgattctggt ggcggtggat    180
catagcggcg tgctgggcta tgcgagcttt ggcgattggc cccgtttga aggctttcgc    240
aacaccgtgg aacatagcgt gtatattcgc ggcgatcagc gcggcaaagg cctgggcccg    300
cagctgatga ccgcgctgat tgcgcgcgcg cgcggctgcg gcaaacatgt gatggtggcg    360
gccattgaaa gcggcaacgc ggcgagcgtg cgcctgcatg aacgcctggg ctttgtggtg    420
accggccaga tgccgcaggt gggcgtgaaa tttggccgct ggctggatct gacctttatg    480
cagctggtgc tggatccggg cgcggaaccg gcgtga                              516
```

<210> SEQ ID NO 8
<211> LENGTH: 492
<212> TYPE: DNA
<213> ORGANISM: Bacillus subtilis

<400> SEQUENCE: 8

```
atgaccctgc gcctggcgga catcgcgat ctggaagcgg tggtggcgat ttataacagc      60
accattgcga gccgcatggt gaccgcggat accgaaccgg tgaccccgga agatcgcatg    120
gaatggttta gcggccatac cgaaagccgc ccgctgtatg tggcggaaga tgaaaacggc    180
```

```
aacgtggcgg cgtggattag cttttgaaacc ttttatggcc gcccggcgta taacaaaacc    240
gcggaagtga gcatttatat tgatgaagcg tgccgcggca aaggcgtggg cagctatctg    300
ctgcaggaag cgctgcgcat tgcgccgaac ctgggcattc gcagcctgat ggcgtttatt    360
tttggccata acaaaccgag cctgaaactg tttgaaaaac atggctttgc ggaatggggc    420
ctgtttccgg gcattgcgga atggatggc aaacgctatg atctgaaaat tctgggccgc    480
gaactgagct ga                                                        492

<210> SEQ ID NO 9
<211> LENGTH: 516
<212> TYPE: DNA
<213> ORGANISM: Enterobacter sp. 638

<400> SEQUENCE: 9
atgatcatcc gccatgccag taaagaagat tgcgccgcta tcggcgagat ttataaccac     60
gccgttgtgc acactgccgc tatctggaat gacaccaccg ttgataccga gaaccgcatt    120
gcgtggtttg aagctcgcac gttgatgggg tatccggtgc tggtcagtga agaaaatggc    180
gtggtcacgg gctatgcgtc atttggcgac tggcgtgcat ttgacggatt tcgccatacg    240
gtcgaacatt cggtctacgt tcaccccgac catcagggca aaggaattgg ccgtgagctg    300
atgaaagcgc tgattggtga agcgcgaaac atcggcaaac acgttatggt ggcgggaatt    360
gaggcacaaa atcacggctc aattcacctg cataagacgc tcggatttgt gattaccggg    420
caaatgccgc aggtcgggac caaatttggc cgctggctgg atctcacctt tatgcagctc    480
cagcttgacg agcgcatcga cccggacgct atctga                              516

<210> SEQ ID NO 10
<211> LENGTH: 528
<212> TYPE: DNA
<213> ORGANISM: Pseudovibrio sp. FO-BEG1

<400> SEQUENCE: 10
atgaaactgc gtcaggcaac caaatctgat cttccgacac ttctggaaat tcacaatgat     60
gccgttaaga cactagctgc gatttggacg gatactttag agacgctgga agatcgagtg    120
agttggttcg aaaagcggat cgcaggcggg tttccgatca ttgtagctga agatgagaac    180
ggcgatgtac ttggctacgg cagttacgga tcttttcgtg aaaaatctgg ttacgataag    240
acggtggagc attctgtcta cgtaaccccg caatcacgcg gtaacggtgc tggctccgtt    300
ttgctggaaa agctgatcga actggcaaaa caggatgatc gccatgtcct tattggcgca    360
atcgacagtg aaaacaaagg ctcaatccgc ctccatgaac gctatggctt caggatcacc    420
ggagaactcc cacaagtcgg cttcaaattc ggccgctggc tggatctcac cctgatgacg    480
cttatcttaa cgatgatga agcaccaaca gcactcgcgc atgaataa                 528

<210> SEQ ID NO 11
<211> LENGTH: 465
<212> TYPE: DNA
<213> ORGANISM: Yarrowia lipolytica PO1f

<400> SEQUENCE: 11
atgaagatat ctccagaacc ctacaccgcc gatttgtaca aattggtgcg caaaaacatg     60
aagggaatgt acgagggttc ggggatgggg tggaataggg ttgacaagat tgacgagatg    120
gaggacgagg agctggcgta tcacgtggct cgcgaaaatg gagagatgct aggattcgtc    180
tcgttcatgc atacggttga agacgacgtg gaggtggtat atctgtatga gcttcaggtg    240
```

```
gccaagggtc gccagggtca cggtgtgggt aaggagctca tgagggttgt gatagacgag    300
gctagggctt gtggtcgtcc gatcatgttg actgttttc tcatgaatga gcgggccatt    360
ggtttctaca ggcggtatgg ttttgagcgg gtggggcggg gtcctcagga gggcaagcgg    420
gtgaggggat ggatgcagat gaggcgagac acgaggagtg actag                   465
```

<210> SEQ ID NO 12
<211> LENGTH: 540
<212> TYPE: DNA
<213> ORGANISM: Corynebacterium glutamicum ATCC 13032

<400> SEQUENCE: 12

```
atggttgaaa gagacttcac tatccgacca atccgcgagg gtgatttccc tcaggtgagg    60
gacatctacg aattgggcct ggagacggga catgcgactt atgagacttc tggtcccacg    120
tgggaccagt tctcccaatc taaaatcatg ataccgtca tggtggcggt agaaaacaac     180
gacccggact tcatcctcgg atgggtgtct gctgctccaa tttcaagccg acaggttttc    240
catggagtgg tggaagattc catctatatc caccccagg gccaaggccg aggaatcggc     300
ggcgctttgc tcgacgccct tatcacctac tgcgaaagca acggcatctg gtcgatccac    360
tcctggatct tcccggaaaa cctcggttct gcgaaactgc atgaatcgaa gggcttcgtg    420
aaggtgggca ccatgcacca aatggcaagg atgccctacg cgagatgga aggacaatgg    480 cgcgattgtg atctgtggga gtgcctctta tccgttccag agcaagctca aagttcctaa    540
```

<210> SEQ ID NO 13
<211> LENGTH: 27
<212> TYPE: DNA
<213> ORGANISM: Artificial Sequence
<220> FEATURE:
<223> OTHER INFORMATION: primer 1

<400> SEQUENCE: 13

```
atccatatga agatatctcc agaaccc                                        27
```

<210> SEQ ID NO 14
<211> LENGTH: 27
<212> TYPE: DNA
<213> ORGANISM: Artificial Sequence
<220> FEATURE:
<223> OTHER INFORMATION: primer 2

<400> SEQUENCE: 14

```
tactctagac tagtcactcc tcgtgtc                                        27
```

<210> SEQ ID NO 15
<211> LENGTH: 26
<212> TYPE: DNA
<213> ORGANISM: Artificial Sequence
<220> FEATURE:
<223> OTHER INFORMATION: primer 3

<400> SEQUENCE: 15

```
atccatatgg ttgaaagaga cttcac                                         26
```

<210> SEQ ID NO 16
<211> LENGTH: 27
<212> TYPE: DNA
<213> ORGANISM: Artificial Sequence
<220> FEATURE:
<223> OTHER INFORMATION: primer 4

-continued

<400> SEQUENCE: 16
tactctagat taggaactttt gagcttg					27

<210> SEQ ID NO 17
<211> LENGTH: 18
<212> TYPE: DNA
<213> ORGANISM: Artificial Sequence
<220> FEATURE:
<223> OTHER INFORMATION: primer 5

<400> SEQUENCE: 17
atcatgagcc atgaaatt					18

<210> SEQ ID NO 18
<211> LENGTH: 24
<212> TYPE: DNA
<213> ORGANISM: Artificial Sequence
<220> FEATURE:
<223> OTHER INFORMATION: primer 6

<400> SEQUENCE: 18
gcactgcagt cacgccggtt ccgc					24

<210> SEQ ID NO 19
<211> LENGTH: 18
<212> TYPE: DNA
<213> ORGANISM: Artificial Sequence
<220> FEATURE:
<223> OTHER INFORMATION: primer 7

<400> SEQUENCE: 19
atcatgaccc tgcgcctg					18

<210> SEQ ID NO 20
<211> LENGTH: 24
<212> TYPE: DNA
<213> ORGANISM: Artificial Sequence
<220> FEATURE:
<223> OTHER INFORMATION: primer 8

<400> SEQUENCE: 20
gcactgcagt cagctcagtt cgcg					24

<210> SEQ ID NO 21
<211> LENGTH: 18
<212> TYPE: DNA
<213> ORGANISM: Artificial Sequence
<220> FEATURE:
<223> OTHER INFORMATION: primer 9

<400> SEQUENCE: 21
atcatgatca tccgccat					18

<210> SEQ ID NO 22
<211> LENGTH: 24
<212> TYPE: DNA
<213> ORGANISM: Artificial Sequence
<220> FEATURE:
<223> OTHER INFORMATION: primer 10

<400> SEQUENCE: 22
gcactgcagt cagatagcgt ccgg					24

<210> SEQ ID NO 23
<211> LENGTH: 18

```
<212> TYPE: DNA
<213> ORGANISM: Artificial Sequence
<220> FEATURE:
<223> OTHER INFORMATION: primer 11

<400> SEQUENCE: 23
atcatgaaac tgcgtcag                                                   18

<210> SEQ ID NO 24
<211> LENGTH: 24
<212> TYPE: DNA
<213> ORGANISM: Artificial Sequence
<220> FEATURE:
<223> OTHER INFORMATION: primer 12

<400> SEQUENCE: 24
gcactgcagt tattcatgcg cgag                                            24

<210> SEQ ID NO 25
<211> LENGTH: 18
<212> TYPE: DNA
<213> ORGANISM: Artificial Sequence
<220> FEATURE:
<223> OTHER INFORMATION: primer 13

<400> SEQUENCE: 25
atcatgaaga tatctcca                                                   18

<210> SEQ ID NO 26
<211> LENGTH: 24
<212> TYPE: DNA
<213> ORGANISM: Artificial Sequence
<220> FEATURE:
<223> OTHER INFORMATION: primer 14

<400> SEQUENCE: 26
gcactgcagc tagtcactcc tcgt                                            24

<210> SEQ ID NO 27
<211> LENGTH: 18
<212> TYPE: DNA
<213> ORGANISM: Artificial Sequence
<220> FEATURE:
<223> OTHER INFORMATION: primer 15

<400> SEQUENCE: 27
atcatggttg aaagagac                                                   18

<210> SEQ ID NO 28
<211> LENGTH: 24
<212> TYPE: DNA
<213> ORGANISM: Artificial Sequence
<220> FEATURE:
<223> OTHER INFORMATION: primer 16

<400> SEQUENCE: 28
gcactgcagt taggaacttt gagc                                            24

<210> SEQ ID NO 29
<211> LENGTH: 24
<212> TYPE: DNA
<213> ORGANISM: Artificial Sequence
<220> FEATURE:
<223> OTHER INFORMATION: primer 17

<400> SEQUENCE: 29
```

```
tgcactagta tgagccatga aatt                                          24

<210> SEQ ID NO 30
<211> LENGTH: 24
<212> TYPE: DNA
<213> ORGANISM: Artificial Sequence
<220> FEATURE:
<223> OTHER INFORMATION: primer 18

<400> SEQUENCE: 30
tgcctcgagt cacgccggtt ccgc                                          24

<210> SEQ ID NO 31
<211> LENGTH: 24
<212> TYPE: DNA
<213> ORGANISM: Artificial Sequence
<220> FEATURE:
<223> OTHER INFORMATION: primer 19

<400> SEQUENCE: 31
tgcactagta tgaccctgcg cctg                                          24

<210> SEQ ID NO 32
<211> LENGTH: 24
<212> TYPE: DNA
<213> ORGANISM: Artificial Sequence
<220> FEATURE:
<223> OTHER INFORMATION: primer 20

<400> SEQUENCE: 32
tgcctcgagt cagctcagtt cgcg                                          24

<210> SEQ ID NO 33
<211> LENGTH: 24
<212> TYPE: DNA
<213> ORGANISM: Artificial Sequence
<220> FEATURE:
<223> OTHER INFORMATION: primer 21

<400> SEQUENCE: 33
tgcactagta tgatcatccg ccat                                          24

<210> SEQ ID NO 34
<211> LENGTH: 24
<212> TYPE: DNA
<213> ORGANISM: Artificial Sequence
<220> FEATURE:
<223> OTHER INFORMATION: primer 22

<400> SEQUENCE: 34
gcactgcagt cagatagcgt ccgg                                          24

<210> SEQ ID NO 35
<211> LENGTH: 24
<212> TYPE: DNA
<213> ORGANISM: Artificial Sequence
<220> FEATURE:
<223> OTHER INFORMATION: primer 23

<400> SEQUENCE: 35
tgcactagta tgaaactgcg tcag                                          24

<210> SEQ ID NO 36
<211> LENGTH: 24
<212> TYPE: DNA
<213> ORGANISM: Artificial Sequence
```

<220> FEATURE:
<223> OTHER INFORMATION: primer 24

<400> SEQUENCE: 36
tgcctcgagt tattcatgcg cgag                                   24

<210> SEQ ID NO 37
<211> LENGTH: 24
<212> TYPE: DNA
<213> ORGANISM: Artificial Sequence
<220> FEATURE:
<223> OTHER INFORMATION: primer 25

<400> SEQUENCE: 37
tgcactagta tgaagatatc tcca                                   24

<210> SEQ ID NO 38
<211> LENGTH: 24
<212> TYPE: DNA
<213> ORGANISM: Artificial Sequence
<220> FEATURE:
<223> OTHER INFORMATION: primer 26

<400> SEQUENCE: 38
tgcctcgagc tagtcactcc tcgt                                   24

<210> SEQ ID NO 39
<211> LENGTH: 24
<212> TYPE: DNA
<213> ORGANISM: Artificial Sequence
<220> FEATURE:
<223> OTHER INFORMATION: primer 27

<400> SEQUENCE: 39
tgcactagta tggttgaaag agac                                   24

<210> SEQ ID NO 40
<211> LENGTH: 24
<212> TYPE: DNA
<213> ORGANISM: Artificial Sequence
<220> FEATURE:
<223> OTHER INFORMATION: primer 28

<400> SEQUENCE: 40
tgcctcgagt taggaacttt gagc                                   24

<210> SEQ ID NO 41
<211> LENGTH: 24
<212> TYPE: DNA
<213> ORGANISM: Artificial Sequence
<220> FEATURE:
<223> OTHER INFORMATION: primer 29

<400> SEQUENCE: 41
tgcggtacca tgagccatga aatt                                   24

<210> SEQ ID NO 42
<211> LENGTH: 24
<212> TYPE: DNA
<213> ORGANISM: Artificial Sequence
<220> FEATURE:
<223> OTHER INFORMATION: primer 30

<400> SEQUENCE: 42
ctaggtacct cacgccggtt ccgc                                   24

```
<210> SEQ ID NO 43
<211> LENGTH: 24
<212> TYPE: DNA
<213> ORGANISM: Artificial Sequence
<220> FEATURE:
<223> OTHER INFORMATION: primer 31

<400> SEQUENCE: 43
tgcggtacca tgaccctgcg cctg                                              24

<210> SEQ ID NO 44
<211> LENGTH: 24
<212> TYPE: DNA
<213> ORGANISM: Artificial Sequence
<220> FEATURE:
<223> OTHER INFORMATION: primer 32

<400> SEQUENCE: 44
ctaggtacct cagctcagtt cgcg                                              24

<210> SEQ ID NO 45
<211> LENGTH: 24
<212> TYPE: DNA
<213> ORGANISM: Artificial Sequence
<220> FEATURE:
<223> OTHER INFORMATION: primer 33

<400> SEQUENCE: 45
tgcggtacca tgatcatccg ccat                                              24

<210> SEQ ID NO 46
<211> LENGTH: 24
<212> TYPE: DNA
<213> ORGANISM: Artificial Sequence
<220> FEATURE:
<223> OTHER INFORMATION: primer 34

<400> SEQUENCE: 46
ctaggtacct cagatagcgt ccgg                                              24

<210> SEQ ID NO 47
<211> LENGTH: 24
<212> TYPE: DNA
<213> ORGANISM: Artificial Sequence
<220> FEATURE:
<223> OTHER INFORMATION: primer 35

<400> SEQUENCE: 47
tgcggtacca tgaaactgcg tcag                                              24

<210> SEQ ID NO 48
<211> LENGTH: 24
<212> TYPE: DNA
<213> ORGANISM: Artificial Sequence
<220> FEATURE:
<223> OTHER INFORMATION: primer 36

<400> SEQUENCE: 48
ctaggtacct tattcatgcg cgag                                              24

<210> SEQ ID NO 49
<211> LENGTH: 24
<212> TYPE: DNA
<213> ORGANISM: Artificial Sequence
<220> FEATURE:
<223> OTHER INFORMATION: primer 37
```

```
<400> SEQUENCE: 49
tgcggtacca tgaagatatc tcca                                          24

<210> SEQ ID NO 50
<211> LENGTH: 24
<212> TYPE: DNA
<213> ORGANISM: Artificial Sequence
<220> FEATURE:
<223> OTHER INFORMATION: primer 38

<400> SEQUENCE: 50
ctaggtaccc tagtcactcc tcgt                                          24

<210> SEQ ID NO 51
<211> LENGTH: 24
<212> TYPE: DNA
<213> ORGANISM: Artificial Sequence
<220> FEATURE:
<223> OTHER INFORMATION: primer 39

<400> SEQUENCE: 51
tgcggtacca tggttgaaag agac                                          24

<210> SEQ ID NO 52
<211> LENGTH: 24
<212> TYPE: DNA
<213> ORGANISM: Artificial Sequence
<220> FEATURE:
<223> OTHER INFORMATION: primer 40

<400> SEQUENCE: 52
ctaggtacct taggaacttt gagc                                          24
```